US009792679B2

(12) United States Patent
Nakazawa et al.

(10) Patent No.: US 9,792,679 B2
(45) Date of Patent: Oct. 17, 2017

(54) DIAGNOSIS ASSISTANCE APPARATUS, DIAGNOSIS ASSISTANCE METHOD, AND COMPUTER READABLE STORAGE MEDIUM

(71) Applicants: NATIONAL CEREBRAL AND CARDIOVASCULAR CENTER, Osaka (JP); Nihon Kohden Corporation, Tokyo (JP)

(72) Inventors: Kazuo Nakazawa, Osaka (JP); Michiaki Iwata, Osaka (JP); Miyuki Hayashi, Tokyo (JP); Tatsuo Yoshida, Tokyo (JP); Tatsuo Nishihara, Tokyo (JP); Koji Takizawa, Tokyo (JP)

(73) Assignees: NATIONAL CEREBRAL AND CARDIOVASCULAR CENTER, Osaka (JP); Nihon Kohden Corporation, Tokyo (JP)

( * ) Notice: Subject to any disclaimer, the term of this patent is extended or adjusted under 35 U.S.C. 154(b) by 89 days.

(21) Appl. No.: 14/299,059

(22) Filed: Jun. 9, 2014

(65) Prior Publication Data

US 2014/0369589 A1    Dec. 18, 2014

(30) Foreign Application Priority Data

Jun. 17, 2013   (JP) ................................. 2013-126719

(51) Int. Cl.
  *G06K 9/00*     (2006.01)
  *G06T 7/00*     (2017.01)
  *G06F 19/00*    (2011.01)

(52) U.S. Cl.
  CPC .......... *G06T 7/0012* (2013.01); *G06F 19/321* (2013.01); *G06F 19/345* (2013.01); *G06F 19/3487* (2013.01)

(58) Field of Classification Search
  CPC combination set(s) only.
  See application file for complete search history.

(56) References Cited

U.S. PATENT DOCUMENTS

2006/0259505 A1    11/2006  Nodate et al.
2010/0016710 A1*    1/2010  Kumar .................. A61B 5/055
                                                    600/425

(Continued)

FOREIGN PATENT DOCUMENTS

JP    2010-39956 A     2/2010
JP    2010-176213 A    8/2010
JP    2012-45419 A     3/2012

OTHER PUBLICATIONS

Communication dated Jul. 15, 2015 issued by the European Patent Office in counterpart European Patent Application No. 14171547.4.

(Continued)

*Primary Examiner* — Tom Y Lu
(74) *Attorney, Agent, or Firm* — Sughrue Mion, PLLC (57) ABSTRACT

A diagnosis assistance apparatus for assisting a diagnosis using schemas includes a storage section that stores a plurality of different schemas each configured by a figure representing a body region, an acquiring section that acquires results of a plurality of examinations that are performed on an examination target, a schema refining section that refines a schema of a body region related to a disease that is predicted from the acquired examination results, from the schemas step-by-step in accordance with progress of the examinations, and a displaying section that displays the schema refined by the schema refining section.

16 Claims, 10 Drawing Sheets

(56) References Cited

U.S. PATENT DOCUMENTS

| | | |
|---|---|---|
| 2010/0034438 A1 | 2/2010 | Iwase |
| 2010/0082699 A1* | 4/2010 | Miyasa ................. G06F 19/321 707/802 |
| 2010/0189323 A1 | 7/2010 | Sakagawa |
| 2013/0093781 A1 | 4/2013 | Suzuki et al. |
| 2013/0338447 A1* | 12/2013 | Gilad-Gilor ............. A61B 5/00 600/300 |
| 2014/0037164 A1 | 2/2014 | Iwase |

OTHER PUBLICATIONS

Office Action dated Jan. 31, 2017 by the Japanese Patent Office in counterpart Japanese Patent Application No. 2013-126719.

* cited by examiner

START OF EXAMINATION

MEASUREMENT DATA

| SITE | IBP | | | SaO2 % |
|---|---|---|---|---|
| | a, s | v, d, b | m. e | |
| | | | | |

LARGE-CLASSIFICATION CANDIDATES
OF CORRESPONDING DISEASE (23)

VSD (10)
ASD (8)
AVSD (2)
PDA (3)
CoA (6)
AS・AR (6)
PS (3)
TOF (4)
TA (5)
⋮

FIG. 6

DURING EXAMINATION

MEASUREMENT DATA

| SITE | IBP | | | SaO2 % |
|---|---|---|---|---|
| | a, s | v, d, b | m. e | |
| PCW | 5 | 6 | 5 | |
| PA | 41 | 18 | 29 | 82 |

LARGE-CLASSIFICATION CANDIDATES
OF CORRESPONDING DISEASE (4)

VSD (10)
ASD (8)
AVSD (2)
PDA (3)

FIG. 7

DURING EXAMINATION

MEASUREMENT DATA

| SITE | IBP | | | SaO2 % |
|---|---|---|---|---|
| | a,s | v, d, b | m. e | |
| PCW | 5 | 6 | 5 | |
| PA | 41 | 18 | 29 | 82 |
| RV | 42 | 5 | 6 | 82 |

PERFORM MEASUREMENT OF RAP

LARGE-CLASSIFICATION CANDIDATES
OF CORRESPONDING DISEASE (3)

VSD (10)
ASD (8)
AVSD (2)

FIG. 8

DURING EXAMINATION

MEASUREMENT DATA

| SITE | IBP | | | SaO2 % |
|---|---|---|---|---|
| | a,s | v, d, b | m. e | |
| PCW | 5 | 6 | 5 | |
| PA | 41 | 18 | 29 | 82 |
| RV | 42 | 5 | 6 | 82 |
| RA | 5 | 3 | 4 | 73 |

LARGE-CLASSIFICATION CANDIDATES
OF CORRESPONDING DISEASE (1)

VSD (10)

PERIMEMBRANOUS PART (3)
        DEFECT OPENING   SMALL
                                        MEDIUM
                                        LARGE     INFUNDIBULAR PART (3)
        AORTIC VALVE PROLAPSE
        AORTIC VALVE REGURGITATION     MUSCULAR PART (4)
        DEFECT OPENING   SMALL
                                        MEDIUM
                                        LARGE         MULTIPLE

FIG. 9

END OF EXAMINATION

MEASUREMENT DATA

| SITE | IBP | | | SaO2 % |
|---|---|---|---|---|
| | a, s | v, d, b | m. e | |
| PCW | 5 | 6 | 5 | |
| PA | 41 | 18 | 29 | 82 |
| RV | 42 | 5 | 6 | 82 |
| RA | 5 | 3 | 4 | 73 |
| LV | 121 | 4 | 6 | 97 |
| Ao | 120 | 78 | 99 | 97 |

FICK
  CO 2.99L/min    SV 28.5ml/BEAT
  CI 4.40L/min/m²   SI 41.9ml/BEAT/m²

OXY
  MV 73.0%  PV 97.0%  PA 82.0%  SA 97.0%
  Qp 4.70L/min  Qs 2.94L/min  Qe 2.94L/min
  Qp/Qs = 1.60

SHUNT  L-R  1.76L/min  37.5%
              R-L  0.0L/min  0.0%

RESISTANCE
  SVR 3156     SVRI 2143
  SVR 3265     TSRI 2217
  SVR  409     SVRI  277
  SVR  409     SVRI  277
  SVR  494     SVRI  335
    (dyn·sec/cm⁵)   (m²·dyn·sec/cm⁵)
  PSR 0.13

LARGE-CLASSIFICATION CANDIDATES
OF CORRESPONDING DISEASE (1)

VSD (5)

PERIMEMBRANOUS PART (2)

DEFECT OPENING
              MEDIUM       DEFECT OPENING
              LARGE   INFUNDIBULAR PART (1)

MUSCULAR PART (2)

DEFECT OPENING
              MEDIUM       DEFECT OPENING
              LARGE

FIG. 10

END OF EXAMINATION

MEASUREMENT DATA

| SITE | IBP | | | SaO2 % |
|---|---|---|---|---|
| | a,s | v, d, b | m. e | |
| PCW | 5 | 6 | 5 | |
| PA | 41 | 18 | 29 | 82 |
| RV | 42 | 5 | 6 | 82 |
| RA | 5 | 3 | 4 | 73 |
| LV | 121 | 4 | 6 | 97 |
| Ao | 120 | 78 | 99 | 97 |

FICK
  CO 2.99L/min    SV 28.5ml/BEAT
  CI 4.40L/min/m$^2$  SI 41.9ml/BEAT/m$^2$ OXY
  MV 73.0%  PV 97.0%  PA 82.0%  SA 97.0%
  Qp 4.70L/min  Qs 2.94L/min  Qe 2.94L/min
  Qp/Qs = 1.60

SHUNT  L-R  1.76L/min  37.5%
               R-L  0.0L/min   0.0%

RESISTANCE
  SVR 3156     SVRI 2143
  SVR 3265     TSRI 2217
  SVR  409     SVRI  277
  SVR  409     SVRI  277
  SVR  494     SVRI  335
    (dyn·sec/cm$^5$)   (m$^2$·dyn·sec/cm$^5$)
  PSR 0.13

LARGE-CLASSIFICATION CANDIDATES
OF CORRESPONDING DISEASE (1)

VSD (5)

PERIMEMBRANOUS PART (2)
    DEFECT OPENING  SMALL
                               MEDIUM

INFUNDIBULAR PART (1)

MUSCULAR PART (2)
    DEFECT OPENING  SMALL
                               MEDIUM

FIG. 11

AFTER EDITING

VSD (MEMBRANOUS PART, DEFECT OPENING: MEDIUM)

MEASUREMENT DATA

| SITE | IBP | | | SaO2 % |
|---|---|---|---|---|
| | a,s | v, d, b | m. e | |
| PCW | 5 | 6 | 5 | |
| PA | 41 | 18 | 29 | 82 |
| RV | 42 | 5 | 6 | 82 |
| RA | 5 | 3 | 4 | 73 |
| LV | 121 | 4 | 6 | 97 |
| Ao | 120 | 78 | 99 | 97 |

RVs/LVs = 0.35

FICK
   CO  2.99L/min     SV  28.5ml/BEAT
   CI  4.40L/min/m²  SI  41.9ml/BEAT/m²

OXY
   MV 73.0%   PV 97.0%  PA 82.0%  SA 97.0%
   Qp 4.70L/min  Qs 2.94L/min  Qe 2.94L/min
   Qp/Qs = 1.60

SHUNT  L-R  1.76L/min  37.5%
               R-L  0.0L/min   0.0%

RESISTANCE
   SVR  3156       SVRI  2143
   SVR  3265       TSRI  2217
   SVR   409       SVRI   277
   SVR   409       SVRI   277
   SVR   494       SVRI   335
    (dyn·sec/cm⁵)   (m²·dyn·sec/cm⁵)
   PSR  0.13

FIG. 12

DURING EXAMINATION

MEASUREMENT DATA

| SITE | IBP | | | SaO2 % |
|---|---|---|---|---|
| | a,s | v, d, b | m, e | |
| PCW | 5 | 6 | 5 | |
| PA | 41 | 18 | 29 | 82 |
| RV | 42 | 5 | 6 | 82 |
| RA | 5 | 3 | 4 | 73 |

INPUT MEASUREMENT VALUE OF
PV SaO2 OR LV SaO2 OR AO SaO2

LARGE-CLASSIFICATION CANDIDATES
OF CORRESPONDING DISEASE (1)

VSD (10)

PERIMEMBRANOUS PART (3)
        DEFECT OPENING   SMALL
                                    MEDIUM
                                    LARGE     INFUNDIBULAR PART (3)
        AORTIC VALVE PROLAPSE
        AORTIC VALVE REGURGITATION     MUSCULAR PART (4)
        DEFECT OPENING   SMALL
                                    MEDIUM
                                  LARGE         MULTIPLE

DIAGNOSIS ASSISTANCE APPARATUS, DIAGNOSIS ASSISTANCE METHOD, AND COMPUTER READABLE STORAGE MEDIUM

CROSS REFERENCE TO RELATED APPLICATION

This application is based on Japanese Patent Applications No. 2013-126719 filed on Jun. 17, 2013, the contents of which are incorporated herein by reference.

BACKGROUND

The presently disclosed subject matter relates to a diagnosis assistance apparatus, a diagnosis assistance method, and a computer readable storage medium.

In a medical institution such as a hospital, conventionally, a doctor performs examinations required for treatment or diagnosis, on a patient, and correctly records results of the examinations. For example, a doctor performs a cardiac catheterization and the like on a patient with cardiac disease, and, manually or through a personal computer, writes results of the examinations in a schema configured by a figure simulating a heart.

In order that, in accordance with the examination results, a schema which is focused on the most relevant disease location, and which represents the disease state can be presented to the patient, a large number of schemas are prepared in which, in accordance with various diseases and severities, disease locations are simulated in many angles while changing perspective. The doctor must select a schema which is most suitable for the disease state of the patient and writing of the examination results, from such a large number of schemas. The work of selecting a schema is not easy for the doctor because the doctor must make a comprehensive determination on the examination results. As a result, the recording of the examination results requires a long time.

Recently, therefore, a technique has been developed in which a large number of schemas are stored in a computer, and a schema is automatically extracted based on examination results. For example, JP-A-2010-176213 discloses a computer-aided diagnosis apparatus which analyzes medical examination data (including medical image data such as X-ray images), and which can automatically extract a schema that is most suitable for writing of examination results.

In JP-A-2010-176213, however, all medical examination data are read at one time, and then a process of extracting a schema is started. When all examinations have not been completed, therefore, a schema for writing examination results cannot be selected.

Some of the examinations require a long time. When a schema cannot be selected until all the examinations are completed, the doctor cannot perform even the preparatory work of writing examination results in a schema, during the intervals between the examinations. Namely, the recording is inefficiently performed. Therefore, there arises a problem in that the recording of examination results requires a long time.

The presently disclosed subject matter has been conducted in view of the above-discussed circumstances. It is an object of the presently disclosed subject matter to provide a diagnosis assistance apparatus, diagnosis assistance method, and a computer readable medium which can reduce the time to produce a schema based on examination results, and complete recording of the examination results.

SUMMARY

In order solve the problem, the diagnosis assistance apparatus of the presently disclosed subject matter which includes a storage section that stores a plurality of different schemas each configured by a figure representing a body region, and which assists a diagnosis using the schemas has: an acquiring section which acquires results of a plurality of examinations that are performed on an examination target; a schema refining section which refines a schema of a body region related to a disease that is predicted from the previously acquired examination results, from the schemas in a stepwise manner in accordance with progress of the examinations; and a displaying section which displays the schema refined by the schema refining section.

According to the presently disclosed subject matter, in accordance with progress of a plurality of examinations on the examination target, the schema of the body region related to the disease of the patient is stepwise refined, and then displayed. According to the configuration, even when all of the examinations have not been completed, the doctor can presume to some extent the completed figure of the schema. Therefore, the doctor can perform a work of, for example, organizing results which are to be recorded in the schema, during the intervals between the examinations. As a result, the time which must elapse before completion of the recording of examination results can be shortened.

The problems, configurations, and effects other than those described above will be clarified in the following description of the embodiment.

DETAILED DESCRIPTION OF EMBODIMENTS

Figure 1:
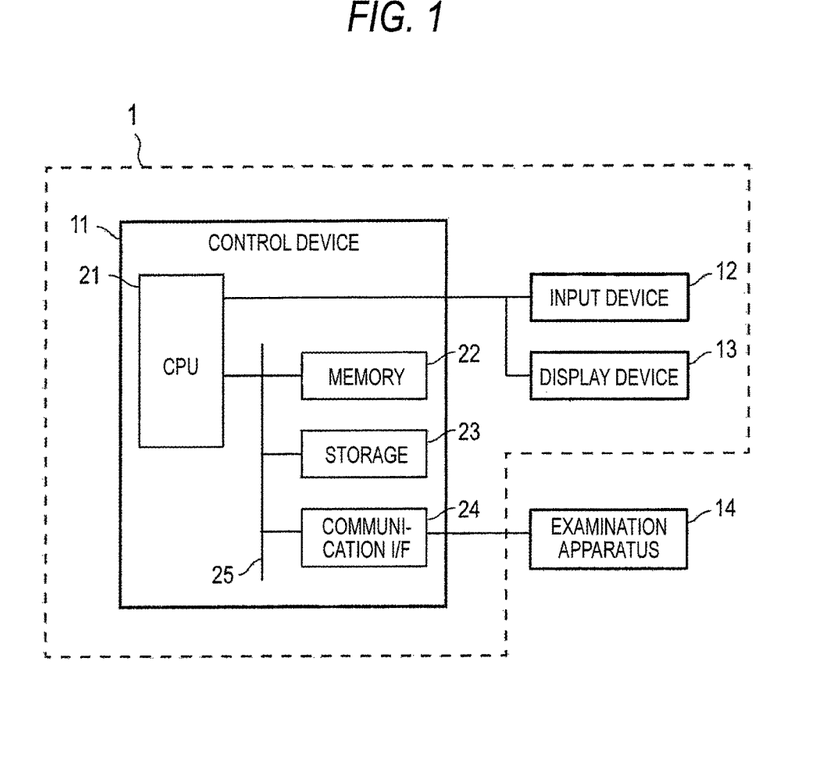
FIG. 1 is a block diagram showing the hardware configuration of a diagnosis assistance apparatus.
Figure 2:
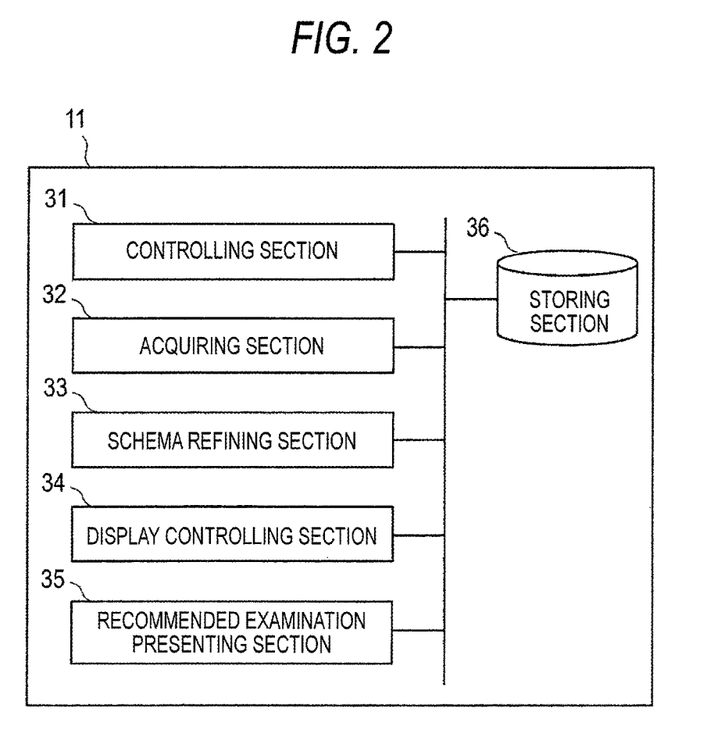
FIG. 2 is a block diagram showing the functional configuration of the diagnosis assistance apparatus.

Hereinafter, an embodiment of the presently disclosed subject matter will be described with reference to the accompanying drawings. In the description of the drawings, the identical components are denoted by the same reference numerals, and duplicated description is omitted. In the drawings, the dimension ratios are exaggerated for the sake of convenience in description, and may be sometimes different from the actual ratios FIG. 1 is a block diagram showing an example of the hardware configuration of a diagnosis assistance apparatus 1 of the embodiment, FIG. 2 is a block diagram showing an example of the functional configuration of the diagnosis assistance apparatus 1, and FIGS. 3A to 3H are views respectively exemplifying schemas to be recorded in the diagnosis assistance apparatus 1.

Hereinafter, the configuration of the diagnosis assistance apparatus 1 will be schematically described with reference to FIGS. 1 to 3H.

<Diagnosis Assistance Apparatus 1>

The diagnosis assistance apparatus 1 assists a doctor to make disease diagnosis, and is configured by a usual computer apparatus in which an application for preparing schemas for rapidly producing an examination result record, and comprehensively informing the patient of the disease state is installed. A schema is formed by image data of a figure simulating a disease location such as organs. Also editing in which data showing examination results or the like are superimposed on a schema may be possible.

As the diagnosis assistance apparatus 1, for example, a desktop PC (Personal Computer) may be used, or a portable terminal such as a tablet terminal, a smart phone, or a mobile phone may be used.

As shown in FIG. 1, the diagnosis assistance apparatus 1 includes a control device 11, an input device 12, and a display device 13, and is connected with an examination apparatus 14.

The control device 11 controls the whole diagnosis assistance apparatus 1. For example, the control device 11 has a CPU (Central Processing Unit) 21, a memory 22, a storage 23, and a communication interface (I/F) 24. These components are interconnected through a bus 25 for exchanging signals.

The CPU 21 is a control circuit configured by a multicore processor which, in accordance with programs, controls the components and executes various calculation processes, and the like. Functions of the diagnosis assistance apparatus 1 are exerted by execution of programs respectively corresponding to the functions by the CPU 21.

The memory 22 is a fast accessible main memory device which functions as a working area to temporarily store programs and data. As the memory 22, for example, a DRAM (Dynamic Random Access Memory), an SDRAM (Synchronous Dynamic Random Access Memory), an SRAM (Static Random Access Memory), or the like may be employed.

The storage 23 is a large-capacity auxiliary memory device which stores various programs including an operating system, and various data. As the storage 23, for example, a flash memory, a solid-state drive, a hard disk, a ROM (Read Only Memory), or the like may be employed.

The communication I/F 24 is an interface for communicating with the examination apparatus 14, and, for example, may be an interface for USB (Universal Serial Bus) communication, BlueTooth, or infrared communication. Alternatively, an interface unique to the manufacturer of the diagnosis assistance apparatus 1 or the examination apparatus 14 may be used.

The input device 12 receives various inputs from the user. As the input device 12, for example, a keyboard, a mouse, or the like may be employed.

The display device 13 displays a screen for displaying imported results of examinations which are performed by using the examination apparatus 14 (hereinafter, the screen is referred to as "result display screen"), etc. As the display device 13, for example, a liquid crystal display, an organic EL (Electro-Luminescence), or the like may be employed.

The examination apparatus 14 is used by a doctor or the like to perform examinations required for diagnosis on the patient, and for example may be an apparatus for performing a cardiac catheterization which is to be applied to a patient with congenital heart disease, or a blood gas analysis of blood collected from the interior of the heart. The examination apparatus 14 may further include devices such as those for measuring the body length and weight of the patient. In a cardiac catheterization, a catheter is percutaneously inserted into a cardiovascular to detect a morphological abnormality by using a contrast agent, or measure the pressure of the cardiac lumen (hereinafter, the pressure is referred to as "intracardiac pressure") and the oxygen saturation to know the hemodynamics. In a blood gas analysis, the amounts (saturations) of oxygen and carbon dioxide contained in blood, and the like, or the amount of hemoglobin are measured. Results of examinations performed by the examination apparatus 14 are transmitted to the diagnosis assistance apparatus 1 through the communication I/F 24.

As shown in FIG. 2, the diagnosis assistance apparatus 1 formed by the above-described hardware configuration has as the functional configuration a controlling section 31, an acquiring section 32, a schema refining section 33, a display controlling section 34, a recommended examination presenting section 35, and a storing section 36.

The controlling section 31 is configured by so-called computer basic software which provides system management of the diagnosis assistance apparatus 1, and a basic user operation environment.

The acquiring section 32 acquires results of a plurality of examinations which are performed on an examination target by the examination apparatus 14. For example, the acquiring section 32 acquires the intracardiac pressure measured by the cardiac catheterization, the oxygen saturation or amount of hemoglobin in blood measured by the blood gas analysis, from the examination apparatus 14. The acquiring section 32 reads data indicating examination results which are output from the examination apparatus 14 (hereinafter, the data are sometimes referred to as "examination result data"), through the communication I/F 24 to acquire the examination results.

The schema refining section 33 refines a schema of a body region related to a disease that is predicted from the previously acquired examination results, from schemas in a stepwise manner in accordance with the progress of the examinations by the examination apparatus 14. At a stage in which a first examination (for example, a measurement of the intracardiac pressure of the a predetermined region of the heart obtained by a cardiac catheterization) is ended, for example, the schema refining section 33 identifies diseases which may possibly cause the result of the first examination, and selects only schemas of body regions related to the identified diseases, from all schemas. However, schemas which are related to the same body regions, but which are not related to the identified diseases are not selected. Thereafter, a second examination (for example, a blood gas analysis of the predetermined body region on which the first examination is performed) is executed. Then, the schema refining section 33 identifies diseases which are identified in the first examination, and which may possibly cause the result of the second examination, and selects schemas of body regions related to the identified diseases. In this way, the schema refining section 33 refines schemas in a stepwise manner in accordance with the progress of the examinations by the examination apparatus 14. The examinations are not limited to the first and second examinations, and may be performed three or more times.

The display controlling section 34 performs a control of displaying the examination result data acquired by the acquiring section 32, and the schemas which are refined by the schema refining section 33, on the display device 13. Each time when examinations are executed on the patient, for example, the display controlling section 34 performs the control of displaying the examination result data and the refined schemas on the display device 13. The detail of the display screen (result display screen) will be described later.

The recommended examination presenting section 35 presents an examination which allows the schemas refined by the schema refining section 33 to be further refined, as a recommended examination. In the case where, when, with respect to the schemas refined by the results of the first and second examinations, measurements of the intracardiac pressure and blood gas analysis of a region of the heart which is different from that in the first and second examinations are additionally performed, diseases can be further limited, and also related schemas can be further refined, for example, the recommended examination presenting section 35 presents the additional examinations to the doctor or the like.

The storing section 36 stores a plurality of different schemas. As exemplarily shown in FIGS. 3A to 3H, for example, the storing section 36 stores various schemas such as (A) a schema in which a normal heart is drawn, (B) a schema in which an abnormal heart in which a hole is formed in the pulmonary artery is drawn, (C) a schema in which an abnormal heart in which the interatrial septum that separates the right atrium from the left atrium from each other is damaged is drawn, (D) a schema in which an abnormal heart in which the interventricular septum that separates the right ventricle and the left ventricle from each other is damaged is drawn, (E) a schema in which an abnormal heart in which the mitral orifice is stenosed is drawn, (F) a schema in which an abnormal heart in which the aorta is connected to the pulmonary artery is drawn, (G) a schema in which an abnormal heart of the single ventricle in which the interventricular septum that is to separate the right ventricle and the left ventricle from each other is not formed is drawn, and (H) a schema in which an abnormal heart (tetralogy of Fallot) in which the pulmonary artery is stenosed, the interventricular septum is damaged, overriding of aorta occurs, and the right ventricle hypertrophies is drawn. Of course, the storing section 36 may store not only schemas in which a heart is drawn, but also schemas in which other organs such as bones and muscles are drawn.

The above-described controlling section 31, schema refining section 33, display controlling section 34, and recommended examination presenting section 35 are realized by the operation of the CPU 21 in which programs installed in the storage 23 are read in the memory 22, and the programs are executed. The acquiring section 32 is realized by reading programs installed in the storage 23, in the memory 22, and executing the programs to control the communication I/F 24. The storing section 36 is realized by the storage 23 and the memory 22.

<Schema Producing Process>

Next, characteristic operations of the diagnosis assistance apparatus 1 will be described.

Figure 4:
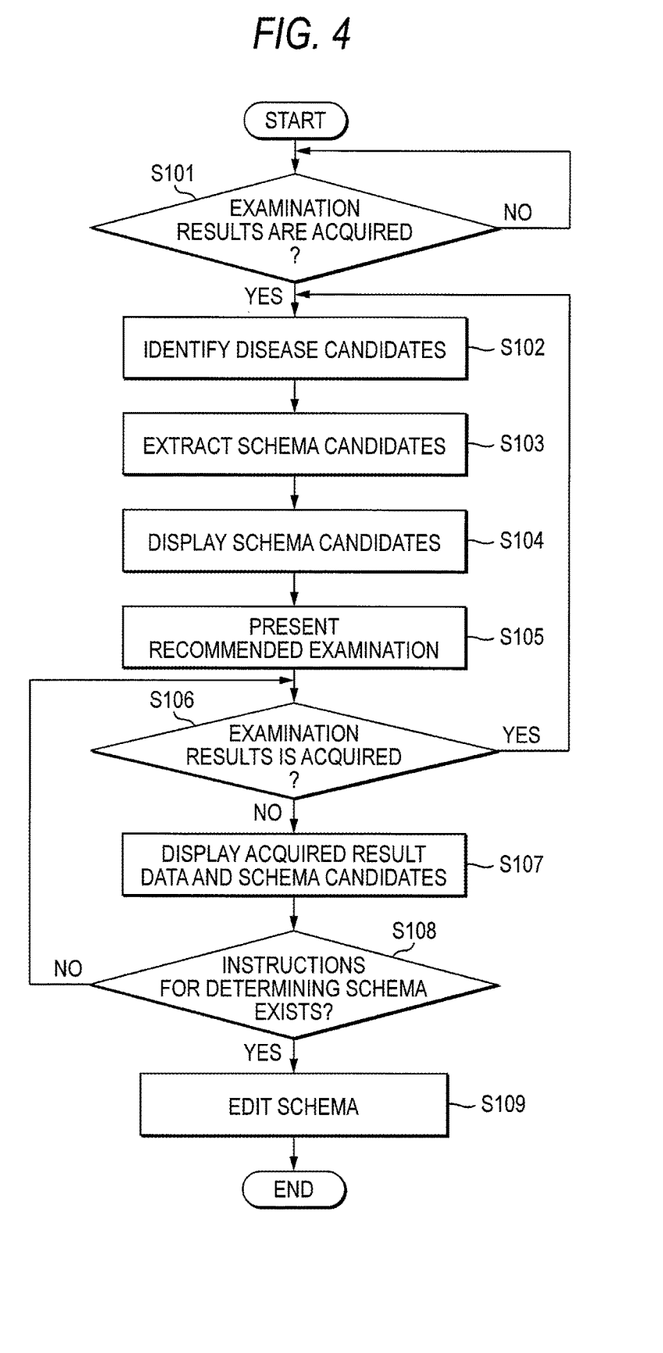
FIG. 4 is a flowchart showing a procedure of a process of producing schemas.
Figure 5:
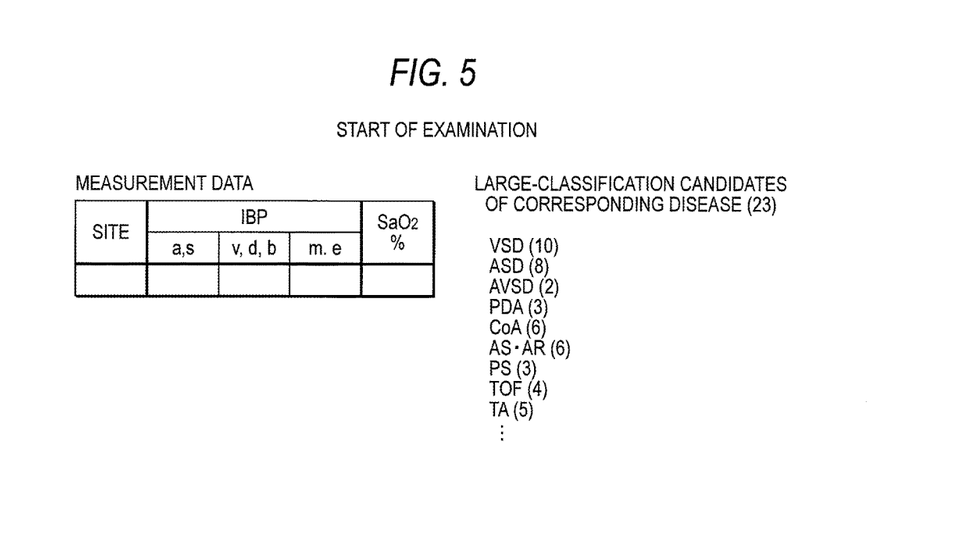
FIG. 5 is a view showing a display example of a result display screen at a timing when the process of producing schemas is started.
Figure 6:
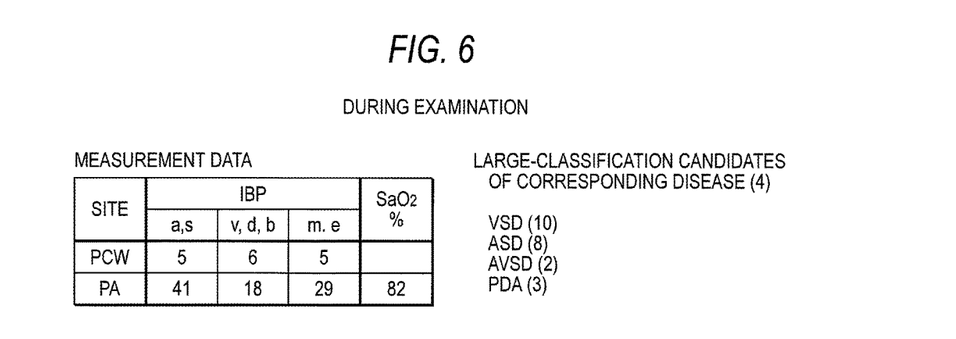
FIG. 6 is a view showing a display example of the result display screen at a stage in which a part of examinations are ended.
Figure 7:
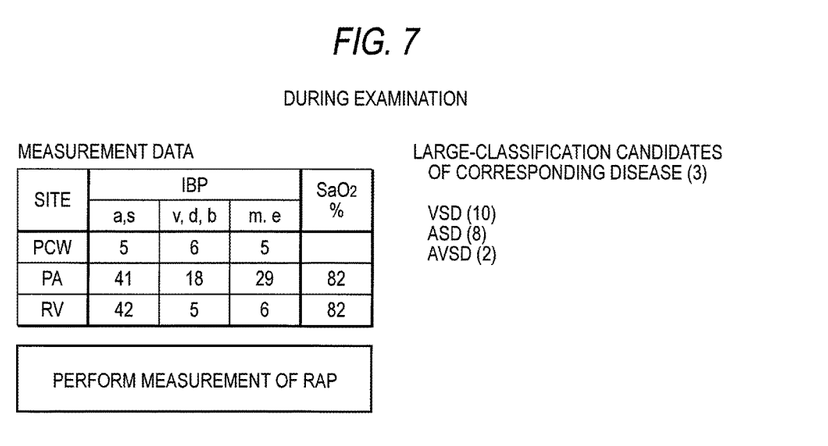
FIG. 7 is a view showing a display example of the result display screen at a stage in which a recommended examination is presented.
Figure 8:
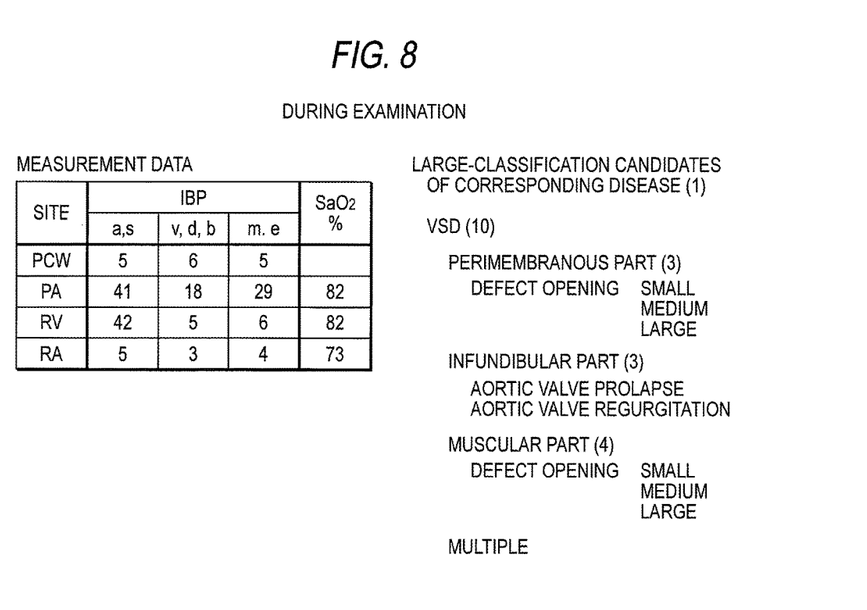
FIG. 8 is a view showing a display example of the result display screen at a stage in which the recommended examinations are ended.
Figure 9:
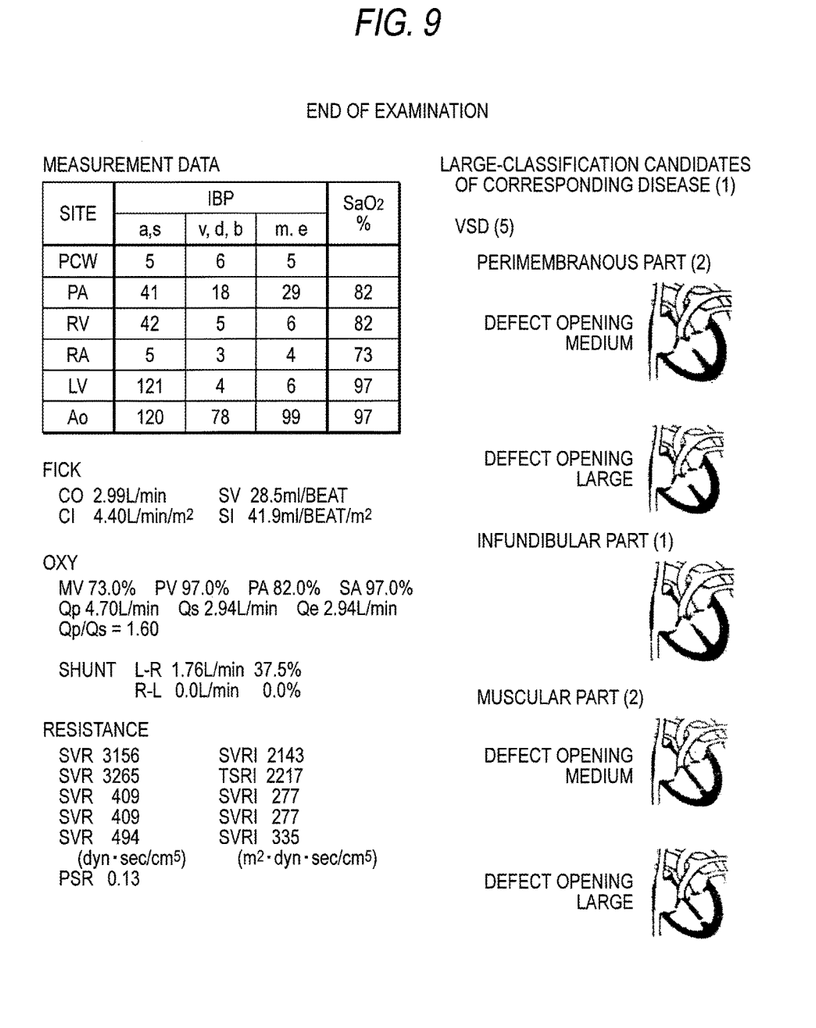
FIG. 9 is a view showing a first display example of the result display screen at a stage in which all the examinations are ended.
Figure 10:
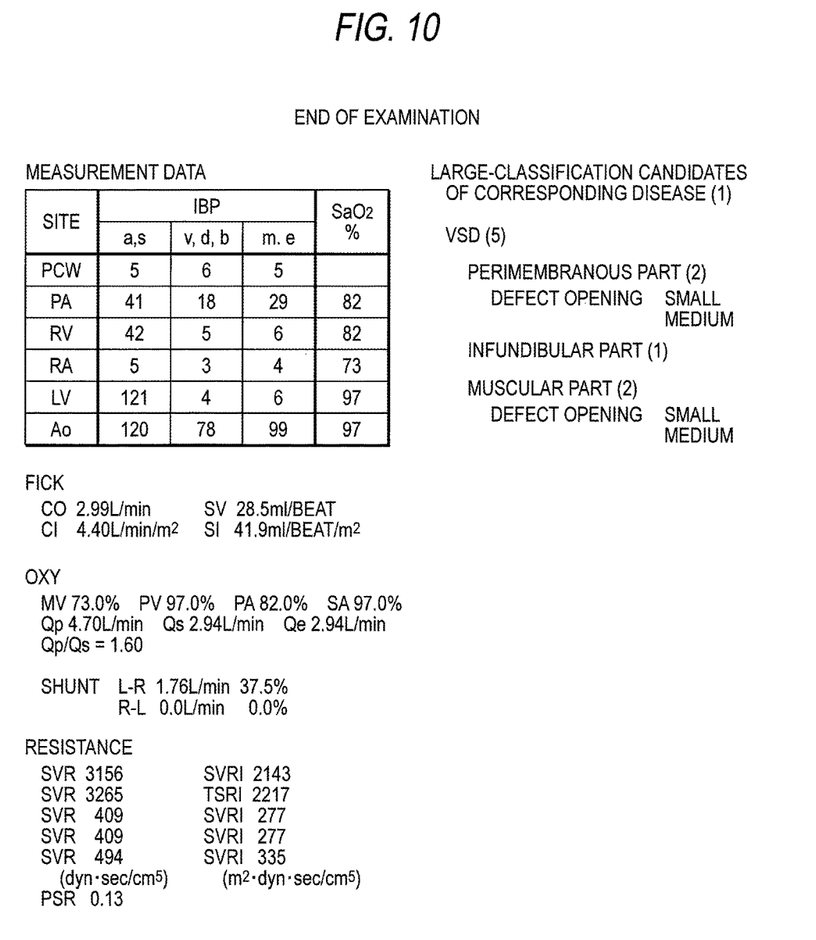
FIG. 10 is a view showing a second display example of the result display screen at the stage in which all the examinations are ended.
Figure 11:
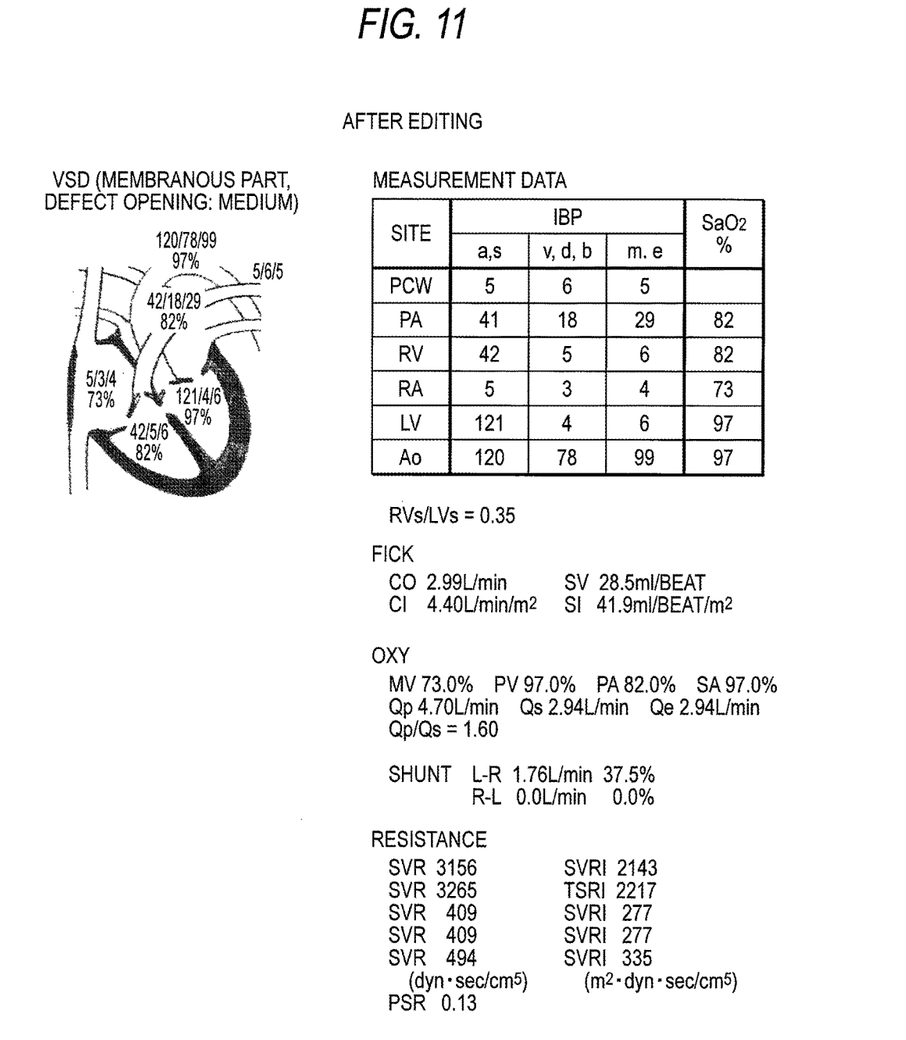
FIG. 11 is a view showing a display example of the result display screen at a timing when data of examination results are written in a schema.

FIG. 4 is a flowchart showing a procedure of a schema producing process which is performed in the diagnosis assistance apparatus 1, and FIGS. 5 to 11 show a transition example of the result display screen which is changed in accordance with the progress of the process of producing schemas. FIG. 5 shows a display example of the result display screen at a timing when the process of producing schemas is started, FIG. 6 shows a display example of the result display screen at a stage in which a part of examinations are ended, FIG. 7 shows a display example of the result display screen at a stage in which a recommended examination is presented, FIG. 8 shows a display example of the result display screen at a stage in which the recommended examination is ended, FIG. 9 shows a first display example of the result display screen at a stage in which all examinations are ended, FIG. 10 shows a second display example of the result display screen at the stage in which all examinations are ended, and FIG. 11 shows a display example of the result display screen at a timing when examination result data are written in a schema.

When the diagnosis assistance apparatus 1 is powered ON at the same time when an examination by the examination apparatus 14 is started, for example, the diagnosis assistance apparatus 1 starts the process of producing schemas shown in FIG. 4.

When the process of producing schemas is started, the display controlling section 34 causes the display device 13 to display the result display screen such as shown in FIG. 5. At the start of the process of producing schemas, no examination has been performed, and therefore columns for displaying examination results (IBP, SaO2, and the like) are in blank. All diseases which are registered in the diagnosis assistance apparatus 1 are previously classified, and keywords (codes such as VSD, ASD, and AVSD) which are used as titles of the classified groups are displayed.

In the result display screen, a result of a measurement of the intracardiac pressure is displayed in the column of the IBP, and that of the oxygen saturation is displayed in the column of the SaO2. In the screen, VSD means the ventricular septal defect, ASD the atrial septal defect, AVSD the complete endocardial defect, PDA the patent ductus arteriosus, CoA the coarctation of aorta, AS the aortic stenosis, AR the aortic regurgitation, PS the pulmonary artery stenosis, TOF the tetralogy of Fallot, and TA the tricuspid atresia. These items of the examination results, and the classifications (titles) of the diseases are mere examples, and the presently disclosed subject matter is not limited to them.

Then, the controlling section 31 determines whether results of examinations performed on the patient are acquired or not (step S101). When the doctor performs the cardiac catheterization on a specific body region (for example, the pulmonary artery wedge PCW) of the patient, for example, the acquiring section 32 acquires examination results (IBP, SaO2, and the like) of the body region which are output from the examination apparatus 14, through the communication I/F 24, and therefore the controlling section 31 determines that examination results of the body region are acquired (step S101: YES).

If it is determined that the acquiring section 32 does not acquire examination results (step S101: NO), the controlling section 31 waits until examination results are acquired.

If the controlling section 31 determines that examination results are acquired, the schema refining section 33 identifies candidates of diseases which may possibly produce the acquired examination results, from the diseases which are previously registered in the diagnosis assistance apparatus 1 (step S102).

In the case where the examination results satisfy Condition 1, for example, the schema refining section 33 identifies "VSD" as a disease candidate. In Condition 1, the systolic pressure sys of the pulmonary artery PA is sys≥132, the diastolic pressure dia≥15, the mean pressure mean≥20, the oxygen saturation SaO2 of the pulmonary artery PA is SaO2≥80, and the systolic pressure sys of the right ventricle RV is sys≥50, and the mean pressure mean≥8.

In the case where the examination results satisfy Condition 2, the schema refining section 33 identifies "ASD" as a disease candidate. In Condition 2, the oxygen saturation SaO2 of the right ventricle RV is SaO2≥80, the oxygen saturation SaO2 of the right atrium RA is SaO2≥80, the pressure gradient PG of (the systolic pressure sys of the pulmonary artery PA − the systolic pressure sys of the right atrium RA) is PG>0, −3<(the mean pressure mean of the right atrium RA−the mean pressure mean of the left atrium LA)<3, the pulmonary to systemic blood flow ratio (Qp/Qs) <1.5, and the oxygen saturation SaO2 of the superior vena cava SVC>the oxygen saturation SaO2 of the inferior vena cava IVC.

In the case where the examination results satisfy Condition 3 the schema refining section 33 identifies "PDA" as a disease candidate. In Condition 3, the systolic pressure sys of the pulmonary artery PA is sys≥30, the diastolic pressure dia≥30, the oxygen saturation SaO2≥80, and the systolic pressure of the right ventricle RV≥30, the mean pressure mean≥8, and the oxygen saturation SaO2≥80.

In the case where the examination results satisfy Condition 4, the schema refining section 33 identifies "TOF" as a disease candidate. In Condition 4, −3<(the diastolic pressure dia of the right ventricle RV−the diastolic pressure dia of the aorta AO)<3, the oxygen saturation SaO2 of the pulmonary artery PA is SaO2≤70, the oxygen saturation SaO2 of the right ventricle RV is SaO2≤70, the oxygen saturation SaO2 of the right atrium RA is SaO2≤70, the oxygen saturation SaO2 of the left atrium LA is SaO2≤95, the oxygen saturation SaO2 of the superior vena cava SVC is SaO2≤70, the oxygen saturation SaO2 of the inferior vena cava IVC is SaO2≤70, the oxygen saturation SaO2 of the left ventricle LV is SaO2≤95, and the oxygen saturation SaO2 of the aorta AO is SaO2≤95.

Figure 3A:
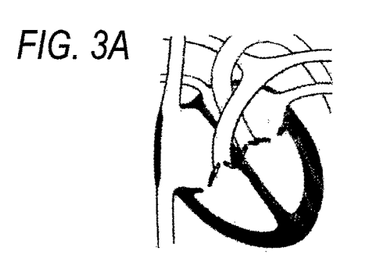
FIGS. 3A to 3H are views respectively exemplifying schemas.
Figure 3B:
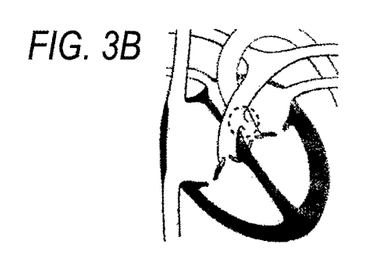
Figure 3C:
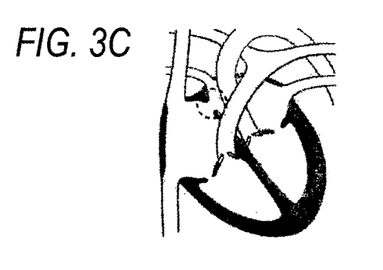
Figure 3D:
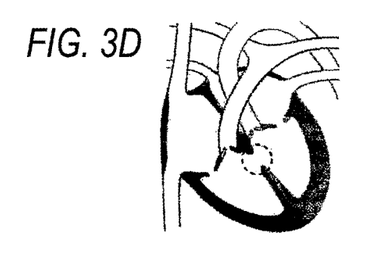
Figure 3E:
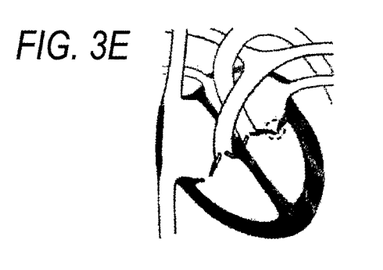
Figure 3F:
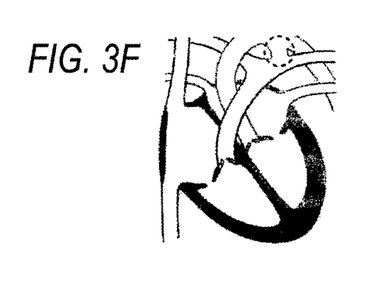
Figure 3G:
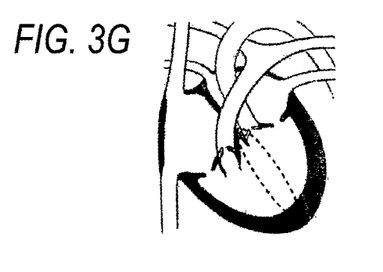
Figure 3H:
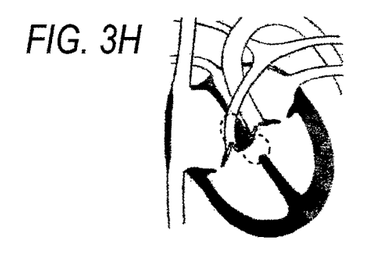

Conditions 1 to 4 above are mere examples, and the presently disclosed subject matter is not limited to them Then, the schema refining section 33 extracts schemas of body regions related to the identified disease candidate, as schema candidates from the storing section 36 (step S103). In the case where "VSD" is identified as the disease candidate in step S102, for example, the schema refining section 33 extracts schemas such as shown in FIGS. 3D and 3G, as related schema candidates. In the case where "ASD" is identified as the disease candidate, a schema such as shown FIG. 3C is extracted as a related schema candidate. In the case where "PDA" is identified as the disease candidate, a schema such as shown FIG. 3F is extracted as a related schema candidate. In the case where "TOF" is identified as the disease candidate, a schema such as shown FIG. 3H is extracted as a related schema candidate.

Next, the display controlling section 34 causes the acquired examination results, and the schema candidates extracted in just before step S103 to be displayed in the result display screen of the display device 13 (step S104). In the case where the number of the schema candidates is larger than a predetermined number (for example, ten), the images of the schema candidates may not be displayed, and the titles (such as VSD, ASD, AVSD, and PDA) of the corresponding diseases may be displayed. FIG. 6 shows an example in which examination results and the titles of diseases are displayed.

Then, the recommended examination presenting section 35 determines whether, with respect to the schemas (candidates) refined in steps S102 and S103, an examination in which further refining is enabled exists or not. If a recommended examination exists, the section presents the recommended examination (step S105). Specifically, the recommended examination presenting section 35 compares conditions for identifying one disease (candidate) such as Conditions 1 to 4 above, with the previously acquired examination results, to search an examination in which there is a possibility that conditions for identifying one disease are satisfied by additional examination.

In the case where, in the first examination, a cardiac catheterization is performed on the pulmonary artery wedge PCW, the pulmonary artery PA, and the right ventricle RV, for example, a measurement examination on the right ventricle RV in which further refining of schemas is enabled is searched.

If it is determined in step S105 that an examination in which schemas can be further refined exists, the recommended examination presenting section 35 causes a message (for example, a character string of "Perform measurement of RAP") for presenting a recommended examination to be displayed in the result display screen as shown in FIG. 7.

At this time, the controlling section 31 determines whether the recommended examination, a previously planned examination, or the like is further performed, and the acquiring section 32 acquires an examinations result or not (step S106). In the case where the recommended examination is performed by the examination apparatus 14, and the acquiring section 32 acquires output examination result data, for example, the controlling section 31 determines that the examination result is acquired.

If it is determined that the examination result is acquired (step S106: YES), the controlling section 31 returns the process to step S102, and again executes the processes of steps S102 and S103.

Then, the display controlling section 34 causes the examination result acquired in step S106 to be additionally displayed in the result display screen of the display device 13, and the schema candidates which are refined in the reprocesses of steps S102 and S103, to be displayed in the screen (step S104).

As far as it is determined in step S106 that a further examination result is acquired, the controlling section 31 repeats the processes of steps S102 to S106.

In the case where, in the examination of the first round, a cardiac catheterization is performed on the pulmonary artery wedge PCW, and it is determined that a result is acquired (step S101: YES), for example, schema candidates are refined by the processes of steps S102 and S103. In step S104, the examination result data in which it is determined in step S101 that the examination result is acquired, and the schema candidates which are extracted in step S103 are displayed in the result display screen of the display device 13. In step S105, then, recommendation of a cardiac catheterization on the pulmonary artery PA, the right ventricle RV, and the right atrium RA is presented.

In the case where, in the examination of the second round, a cardiac catheterization is performed on the pulmonary artery PA, and it is determined that a result is acquired (step S106: YES), the process returns to step S102. The disease candidates and related schema candidates are further refined in the processes of steps S102 and S103 of the second round. In step S104, the examination result data which are acquired in just before step S106 are additionally displayed, and the schema candidates which are refined in just before steps S102 and S103 are displayed in the result display screen of the display device 13. In step S105, then, recommendation of a cardiac catheterization on the right ventricle RV and the right atrium RA is presented.

In the case where, in the examination of the third round, a cardiac catheterization is performed on the right ventricle RV, and it is determined that a result is acquired (step S106: YES), the process returns to step S102 to again repeat the processes of steps S102 to S106.

In the case where, as in the above-described example, examination results are acquired in step S101 and a plurality of processes of step S106, and the identified schema candidates are further refined to a smaller number in steps S102 and S103, schema candidates and titles which indicate the disease state in more detail may be displayed in step S104 in the result display screen of the display device 13. In the case where the number of the schema candidates is larger than a predetermined number (for example, ten), the images of the schema candidates may not be displayed, and the corresponding detailed titles (such as Membranous part, Infundibular part, and Muscular part) may be displayed.

FIG. 8 shows an example in which examination results and detailed titles of diseases are displayed. These displays are mere examples, and the presently disclosed subject matter is not limited to them.

In the case where, in the examination of the first round, "VSD" is identified as a disease candidate, and, in the examination of the second round, examination results satisfying additional conditions of (the systolic pressure sys of the right ventricle RV or the pulmonary artery PA/the systolic pressure sys of the aorta AO or the left ventricle LV)<0.75 and the pulmonary to systemic blood flow ratio (Qp/Qs)<1.5 are further obtained, for example, schemas are refined to a schema (FIG. 3D) in which a defect opening has a medium or smaller size.

In the case where, in the examination of the first round, "VSD" is identified as a disease candidate, and, in the examination of the second round, examination results satisfying additional conditions of (the systolic pressure sys of the right ventricle RV or the pulmonary artery PA/the systolic pressure sys of the aorta AO or the left ventricle LV)≥0.75 and the pulmonary to systemic blood flow ratio (Qp/Qs)≥1.5 are further obtained, for example, schemas are refined to a schema (FIG. 3G) in which a defect opening has a large size.

In the case where, in the examination of the first round, "VSD" is identified as a disease candidate, and, in the examination of the second round, examination results satisfying additional conditions of the pressure gradient PG of (the inflow part inflow of the right ventricle RV-the outflow part outflow of the right ventricle RV)<-3 or PG of (the inflow part inflow of the right ventricle RV-the outflow part outflow of the right ventricle RV)>3 are further obtained, for example, schemas are refined to a schema (not shown) of the double-chambered right ventricle.

In the case where, in the examination of the first round, "PDA" is identified as a disease candidate, and, in the examination of the second round, examination results satisfying additional conditions of the pressure gradient PG of (the diastolic pressure dia of the pulmonary artery PA-the diastolic pressure dia of the aorta AO)>-3 or PG of (the diastolic pressure dia of the pulmonary artery P-the diastolic pressure dia of the aorta AO)<3, and the end-diastolic pressure edp of the left ventricle LV is edp≥10 are further obtained, for example, schemas are refined to a schema (not shown) in which the patent ductus arteriosus is large.

These refinements are mere examples, and the presently disclosed subject matter is not limited to them.

When recommended examinations such as described above are performed, schema candidates can be further refined, and a schema which is highly necessary for the doctor can be rapidly selected.

In the case where the recommended examination is not presented in step S105, or the case where, even when the recommended examination is presented in step S105, it is determined in step S106 that the examination result is not acquired (step S106: NO), the diagnosis assistance apparatus 1 proceeds the process to step S107.

As shown in FIGS. 9 and 10, then the display controlling section 34 causes all examination results which are used in the refinements of schemas, and other examination results to be displayed in the result display screen. Furthermore, the diagnosis assistance apparatus 1 causes at least one of images (FIG. 9) of schema candidates which are finally refined, and titles (FIGS. 9 and 10) of corresponding diseases to be displayed in the result display screen.

In the case where the controlling section 31 receives instructions for selecting one schema from the at least one or more schema candidates, the controlling section 31 determines the schema which is to be used in diagnosis and the like of the patient (step S108: YES). When, during the display of the result display screen shown in FIG. 9 or 10, an operation of selecting one of the schemas is made through the input device 12, for example, the diagnosis assistance apparatus 1 determines the selected schema as the schema which is to be used in diagnosis and the like of the patient.

If instructions for selecting a schema is not input in step S108 (step S108: NO), the diagnosis assistance apparatus 1 returns to step S106 to repeat the processes of steps S106 to S108.

After one of the schemas is selected in step S108 (step S108: YES), the diagnosis assistance apparatus 1 edits the determined schema based on instructions from the doctor or the like (step S109). For example, editing in which examination result data are superimposed on the schema as shown in FIG. 11 is performed.

For example, thereafter, the edited schema and the examination results are printed while being combined with each other, thereby completing the recording of examination results.

Then, the diagnosis assistance apparatus 1 terminates the schema producing process.

When the above-described schema producing process is performed in the diagnosis assistance apparatus 1 in accordance with the progress of the plurality of examinations, disease candidates for the patient are stepwise refined. Together with this, schema candidates or titles of diseases related to the refined disease candidates are displayed. According to the configuration, even when all of the examinations have not been completed, the doctor can presume to some extent the completed figure of the schema from the schema candidates or the disease titles. Before all the examinations are ended, therefore, the doctor can perform a work of, for example, organizing record results which are to be written in a schema. As a result, the time which must elapse before completion of the recording of examination results can be shortened.

As compared with the case where a schema is manually produced, the operability of the schema production is remarkably improved. For example, therefore, incorrect diagnosis due to erroneous writing of examination results or erroneous reading by the doctor can be prevented from occurring. This leads to improved quality of medical care.

As shown in FIG. 7, a recommended examination which enables further refining of schemas may be presented to the doctor (navigation function). This can assist in determination by the doctor which examination should be next performed. Therefore, errors in determination by the doctor can be reduced.

The process units of the above-described flowchart are ones resulting from segmentation of processing in accordance with the main process contents in order to facilitate understanding of the diagnosis assistance apparatus 1. The presently disclosed subject matter is not limited by the classification manner and names of the process steps. The processes performed in the diagnosis assistance apparatus 1 may be further segmented into a larger number of process steps. In one process step, moreover, a larger number of processes may be performed.

<Modifications>

In addition, the above-described embodiment is intended to exemplify the gist of the presently disclosed subject matter, and does not limit the scope of the presently disclosed subject matter. Many alternatives, modifications, and changes are obvious to those skilled in the art.

In the embodiment, the communication I/F 24 is an interface for BlueTooth, infrared communication, or USB communication. However, the presently disclosed subject matter is not limited to this. The communication I/F 24 may be an interface for communicating with the examination apparatus 14 through a computer network such as a LAN (Local Area Network) or the Internet. In this case, a standard such as Ethernet (registered trademark), Wi-Fi (Wireless Fidelity), Token Ring, or FDDI is used.

Although, in the embodiment, a disease related to the heart is set as the examination target, it is a matter of course that the presently disclosed subject matter is directed to also other body regions and diseases.

In the embodiment, the examination apparatus 14 is an apparatus which is independent from the diagnosis assistance apparatus 1. However, the presently disclosed subject matter is not limited to this form. For example, the examination apparatus 14 may be an apparatus which is included in the diagnosis assistance apparatus 1, or the function of the diagnosis assistance apparatus 1 may be incorporated in the examination apparatus 14.

In the embodiment, the acquiring section 32 receives the examination result data which are output from the examination apparatus 14, whereby results of examinations which are performed by using the examination apparatus 14 are supplied to the diagnosis assistance apparatus 1. However, the presently disclosed subject matter is not limited to this. The acquiring section 32 may acquire through the communication I/F 24 the examination result data which are supplied from the examination apparatus 14 to an external storage such as a server or a NAS through a computer network. Alternatively, the user may transfer the examination result data stored in the examination apparatus 14 to a portable memory such as a USB memory, and then input the data in the diagnosis assistance apparatus 1. Alternatively, the user may manually input examination results in the diagnosis assistance apparatus 1, by using the input device 12. These configurations may be used while being combined with each other.

In the embodiment, during a period when the schema producing process is performed, the result display screen is displayed on the display device 13. However, the presently disclosed subject matter is not limited to this. During a period when programs for operating the diagnosis assistance apparatus 1 are active, the processes of steps S101 to S106 may be repeatedly performed irrespective of whether the result display screen is displayed on the display device 13 or not. At any stage, alternatively, the result display screen may be displayed as needed on the display device 13 in response to instructions issued by the user using the input device 12.

In the embodiment, in the case where identified diseases are refined to a smaller number of diseases, schema candidates and titles which indicate the disease state in more detail may be displayed in the result display screen of the display device 13. However, the presently disclosed subject matter is not limited to this. Also at a stage where the disease is not identified, or in the case where a large number of identified diseases exist, with respect to arbitrary ones of the titles of the identified diseases, schema candidates and titles which indicate the disease state in more detail may be displayed in response to instructions through the input device 12, in the result display screen of the display device 13.

Figure 12:
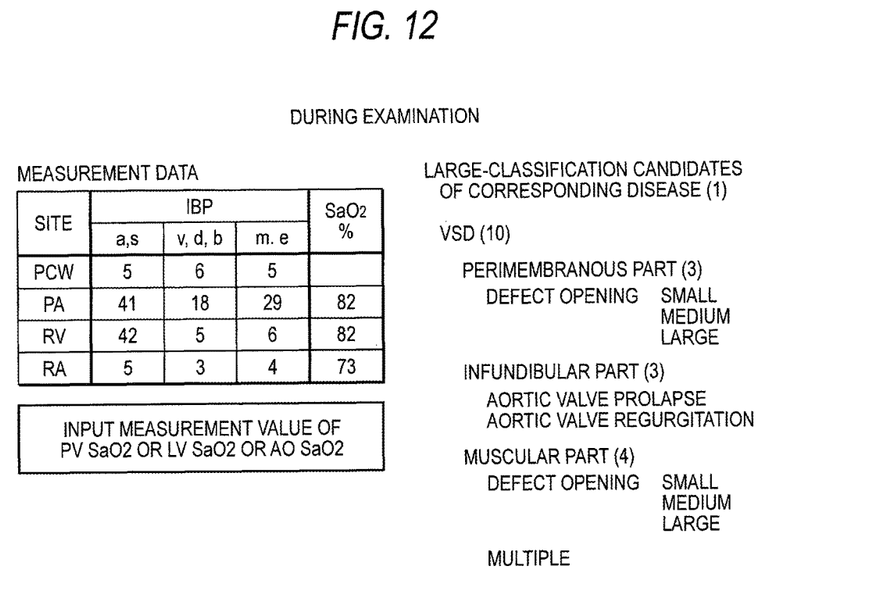
FIG. 12 is a view showing a display example of the result display screen in which a message for requesting a manual input of measurement values (examination results) that can cause schemas to be further refined.

In the embodiment, in the case where an examination in which schemas can be further refined exists, a message for presenting a recommended examination is displayed in the result display screen as shown in FIG. 7. However, the presently disclosed subject matter is not limited to this. Alternatively, at least one of the message for presenting a recommended examination, and that for requesting a manual input of measurement values (examination results) may be displayed. FIG. 12 shows a display example of the result display screen in which a message for requesting a manual input of measurement values (examination results) that can cause schemas to be further refined is displayed. As shown in FIG. 12, the diagnosis assistance apparatus 1 may cause a message for requesting a manual input of measurement values that can cause schemas to be further refined, to be displayed in the result display screen. For example, the diagnosis assistance apparatus 1 may cause a message such as "Input measurement value of RV SaO2 or LV SaO2 or AO SaO2" to be displayed on the result display screen.

In the embodiment, in the case where an examination in which schemas can be further refined exists, a message for presenting a recommended examination or requesting a manual input of measurement values (examination results) is displayed in the result display screen as shown in FIGS. 7 and 12, and acquisition of a result of the recommended examination or that of requested measurement values is determined. However, the presently disclosed subject matter is not limited to this. Alternatively, measurement result data other than the recommended examination or the requested measurement values may be acquired.

In the embodiment, disease candidates are identified based on previously acquired examination results, and then schema candidates related to the disease candidates are extracted. However, the presently disclosed subject matter is not limited to this. While not identifying disease candidates, alternatively, schema candidates may be directly extracted from the previously acquired examination result.

In the embodiment, as the work of editing schemas, only the work in which examination result data are superimposed on the schema in step S109 has been described. However, the presently disclosed subject matter is not limited to this. A work of processing a part of a figure showing a body region, that of coloring figures with different colors in accordance with the values of the examination results such as the oxygen saturation, that of superimposing arrows simply indicating blood flows, or the like on a schema, and other works may be included in the editing work.

In the embodiment, at a stage where all examinations are ended (step S107 above), the diagnosis assistance apparatus 1 receives instructions for selecting one schema. However, the presently disclosed subject matter is not limited to this. Even before all examinations are ended (for example, at the timing when the first examination is ended, or in the middle of the examination), the apparatus may receive instructions for selecting one schema. According to the configuration, when a schema to be selected is already clearly determined before all examinations are ended, the doctor can immediately determine one schema without waiting the ends of all examinations. As a result, the time which must elapse before completion of the recording of examination results in a schema can be further shortened.

The functional configurations of the above-described diagnosis assistance apparatus 1 are ones resulting from classification of processing in accordance with the main process contents in order to facilitate understanding of the functional configurations. The presently disclosed subject matter is not limited by the classification manner and names of the functional configurations. The functional configurations may be further classified into a larger number of functional configurations. Moreover, one functional configuration may be classified so as to perform a larger number of processes.

The programs for operating the diagnosis assistance apparatus 1 may be provided by a computer-readable record medium such as a USB memory, a flexible disk, or a CD-ROM, or online provided through a network such as the Internet. In this case, a program recorded on a computer-readable record medium is usually transferred to and stored in the memory 22, the storage 23, or the like. The program may be provided in the form of a standalone application software, or installed in software of the corresponding device to exert one function of the diagnosis assistance apparatus I.

The processing of each of the above-described components may be realized by a dedicated hardware circuit. In this case, the processing may be executed by a single hardware device, or by a plurality of hardware devices.

What is claimed is:

1. A diagnosis assistance apparatus for assisting a diagnosis using schemas during a plurality of examinations which are continuously performed on an examination target, comprising:
    a memory that stores a plurality of different schemas each configured by a figure representing a body region; and
    a processor configured to execute instructions comprising:
        acquiring results of the plurality of examinations;
        refining a schema of a body region related to a disease that is predicted from the acquired examination results, from the schemas in a middle of the plurality of the examinations; and
        controlling to display the schema refined by the schema refining section,
    wherein the schema is an anatomic drawing formed by simulating a structure of a human body and simplifying the structure.

2. The diagnosis assistance apparatus according to claim 1, wherein the executed instructions further comprise presenting an examination by which further refining is enabled with respect to the refined schemas.

3. The diagnosis assistance apparatus according to claim 1, wherein the acquired examination results comprise at least one from among a blood oxygen saturation, a blood oxygen concentration, a blood carbon dioxide concentration, an amount of hemoglobin, and an intracardiac pressure.

4. The diagnosis assistance apparatus according to claim 1, wherein the executed instructions further comprise receiving selection of one schema from a plurality of schemas that are refined, before all examinations are ended.

5. A diagnosis assistance method which assists a diagnosis using a plurality of different schemas during a plurality of examinations which are continuously performed on an examination target, each configured by a figure representing a body region, the method comprising:
    acquiring examination results of the plurality of examinations;
    refining a schema of a body region related to a disease that is predicted from the acquired examination results, from the schemas in a middle of the plurality of the examinations; and
    displaying the schema refined in refining step,
    wherein the schema is an anatomic drawing formed by simulating a structure of a human body and simplifying the structure.

6. The diagnosis assistance method according to claim 5, further comprising presenting an examination by which further refining is enabled with respect to schemas refined in the schema refining step.

7. The diagnosis assistance method according to claim 5, wherein the examination results acquired in the acquiring step include at least one of a blood oxygen saturation, a blood oxygen concentration, a blood carbon dioxide concentration, an amount of hemoglobin, and an intracardiac pressure.

8. A non-transitory computer readable storage medium that stores a diagnosis assistance program causing a computer system to perform a process for assisting a diagnosis using a plurality of different schemas during a plurality of examinations which are continuously performed on an examination target, each configured by a figure representing a body region, the process comprising:
    acquiring examination results of the plurality of examinations;
    refining a schema of a body region related to a disease that is predicted from the acquired examination results, from the schemas in a middle of the plurality of the examinations; and
    displaying the schema refined in refining step,
    wherein the schema is an anatomic drawing formed by simulating a structure of a human body and simplifying the structure.

9. The non-transitory computer readable storage medium according to claim 8, wherein the process further includes presenting an examination by which further refining is enabled with respect to schemas refined in the schema refining step.

10. The non-transitory computer readable storage medium according to claim 8, wherein the examination results acquired in the acquiring step include at least one of a blood oxygen saturation, a blood oxygen concentration, a blood carbon dioxide concentration, an amount of hemoglobin, and an intracardiac pressure.

11. The diagnosis assistance apparatus according to claim 2, wherein the acquired examination results include at least one of a blood oxygen saturation, a blood oxygen concentration, a blood carbon dioxide concentration, an amount of hemoglobin, and an intracardiac pressure.

12. The diagnosis assistance apparatus according to claim 2, wherein the executed instructions further comprises receiving a selection of one schema from a plurality of schemas that are refined, before all examinations are ended.

13. The diagnosis assistance apparatus according to claim 3, wherein the executed instructions further comprises receiving a selection of one schema from a plurality of schemas that are refined, before all examinations are ended.

14. The diagnosis assistance apparatus according to claim 11, wherein the executed instructions further comprises receiving a selection of one schema from a plurality of schemas that are refined, before all examinations are ended.

15. The diagnosis assistance method according to claim 6, wherein the examination results acquired in the acquiring step include at least one of a blood oxygen saturation, a blood oxygen concentration, a blood carbon dioxide concentration, an amount of hemoglobin, and an intracardiac pressure.

16. The non-transitory computer readable storage medium according to claim 9, wherein the examination results acquired in the acquiring step include at least one of a blood oxygen saturation, a blood oxygen concentration, a blood carbon dioxide concentration, an amount of hemoglobin, and an intracardiac pressure.

* * * * *